United States Patent
Morgan et al.

(10) Patent No.: US 6,238,901 B1
(45) Date of Patent: May 29, 2001

(54) **TYPE II RESTRICTION ENDONUCLEASE, HPY 188 III, OBTAINABLE FROM *HELICOBACTER PYLORI* J188 AND A PROCESS FOR PRODUCING THE SAME**

(75) Inventors: Richard D. Morgan, Middleton, MA (US); Qing Xu, Nashville, TN (US)

(73) Assignees: New England Biolabs, Inc., Beverly, MA (US); Vanderbilt University, Nashville, TN (US)

(*) Notice: Subject to any disclaimer, the term of this patent is extended or adjusted under 35 U.S.C. 154(b) by 0 days.

(21) Appl. No.: 09/401,869

(22) Filed: Sep. 23, 1999

(51) Int. Cl.$^7$ ............... C12N 9/10; C12N 9/22; C12N 15/54; C12N 15/55

(52) U.S. Cl. .............. 435/193; 435/199; 435/252.3; 435/320.1; 536/23.2

(58) Field of Search .................. 435/194, 320.1, 435/252.3, 193; 536/23.2

(56) References Cited

U.S. PATENT DOCUMENTS 5,200,333   4/1993   Wilson ............... 435/172.3

OTHER PUBLICATIONS

Alm, et al. (1999) Nature 397, 176–180. Erratum (1999) Nature 397, 719.*
Endow, et al., J. Mol. Biol. 112:521 (1977).
Waalwijk, et al., Nucleic Acids Res., 5:3231 (1978).
Gingeras, et al., Proc. Natl. Acad. Sci., 80:402 (1983).
Gingeras, et al., Nucleic Acids Res. 5:4105 (1978).
Sanger, et al., Proc. Natl. Acad. Sci., 74:5463 (1977).
Brown, et al., J. Mol. 140:143 (1980).
Deverenx, et al., Nucleic Acids Res. 12:387 (1984).
Schildkraut, Genetic Engineering vol. 6, 117–139, J.K. Setlow and A. Hollaener, eds. (1984).

* cited by examiner

Primary Examiner—Charles L. Patterson, Jr.
(74) Attorney, Agent, or Firm—Gregory D. Williams (57) ABSTRACT

In accordance with the present invention, there is provided a novel restriction endonuclease and its DNA obtainable from *Helicobacter pylori* J188 (NEB#1174), hereinafter referred to as "Hpy188III", which endonuclease:

(1) recognizes the nucleotide sequence 5'-TCNNGA-3' in a double-stranded DNA molecule as shown below,

5'-TC↓NNGA-3'

3'-AGNN↑CT-5'

(wherein G represents guanine, C represents cytosine, A represents adenine, T represents thymine and N represents either G, C, A, or T);

(2) cleaves said sequence in the phosphodiester bonds between the C and first unspecified nucleotide N as indicated with the arrows; and (3) cleaves double-stranded PhiX174 DNA to produce 26 fragments, including fragments of 704, 560, 497, 477, 423, 309, 308, 304, 261, 225 basepairs, and 16 fragments smaller than 200 basepairs.

10 Claims, 3 Drawing Sheets

```
         10              30              50
   GATCCTAAAAAAATTCTACCCAAGCCCGGGCAAAATCACTGAATGGATCGCCCCTGGTGGC
 1 ---------+---------+---------+---------+---------+---------+  60

70              90             110
   GTGAATGTGCGCCTTGATTCGCACGCGCATGCCAATTATGTCGTGCCTACGCACTATGAT
61 ---------+---------+---------+---------+---------+---------+ 120

130             150             170
   TCTATGATAGGCAAGCTCATTGTGTGGGGTGAAAACAGAGAAAGAGCGATCGCTAAGATG
121 ---------+---------+---------+---------+---------+---------+ 180

190             210             230
   AAAAGGGCTTTAAAGGAATTTAAAGTAGAAGGCATTAAAACGACCATTCCTTTTCATATT
181 ---------+---------+---------+---------+---------+---------+ 240

250             270             290
   GAAATGCTTGAAAATGCGGATTTCAGGCAAGCAAAAATCCACACGAAGTATTTAGAAGAA
241 ---------+---------+---------+---------+---------+---------+ 300

310             330             350
   AATTTTTAAGTTTTAAGGATTTTCTTAAGCATGATTTAAGGATTTTAAGCGGTGGGAAGG
301 ---------+---------+---------+---------+---------+---------+ 360

370             390             410
   AATCGGCATTAAGTTTTATAATTTTGTAGTAAAATTTTTTCATGCAAACCCTGTTTAAAG
361 ---------+---------+---------+---------+---------+---------+ 420
                                              M  Q  T  L  F  K  E 430             450             470
   AAATTACCCCTAAACGCTATGTCAATGGCAATGAGATGAAAGAAAATTCTAGCAATGTTC
421 ---------+---------+---------+---------+---------+---------+ 480
    I  T  P  K  R  Y  V  N  G  N  E  M  K  E  N  S  S  N  V  L 490             510             530
   TAGATCAGTATTTCACTAAACCTAGTGTGGCTTTAAAATGCTTCCAAAAAGCTTGTGAAG
481 ---------+---------+---------+---------+---------+---------+ 540
    D  Q  Y  F  T  K  P  S  V  A  L  K  C  F  Q  K  A  C  E  V 550             570             590
   TTATTAAAAAATACGAAAATCCAGATGACTTTATTTTTTTAGAGCCAAGCGCAGGCGATG
541 ---------+---------+---------+---------+---------+---------+ 600
    I  K  K  Y  E  N  P  D  D  F  I  F  L  E  P  S  A  G  D  G 610             630             650
   GGGTGTTTTATGACTTATTCCCTAAAAATAGACGCATCGGTATAGATATTGAACCTAAAA
601 ---------+---------+---------+---------+---------+---------+ 660
    V  F  Y  D  L  F  P  K  N  R  R  I  G  I  D  I  E  P  K  R 670             690             710
   GAGATGGATTTATTCAATGCGATTTTTTAAATTATAAATTGCCTGCGCATCAAAAAGTGA
661 ---------+---------+---------+---------+---------+---------+ 720
    D  G  F  I  Q  C  D  F  L  N  Y  K  L  P  A  H  Q  K  V  I

730
   TTTGCTTGGGCAACCCTCCTTTTGGG
721 ---------+---------+------ 746
    C  L  G  N  P  P  F  G
```

TYPE II RESTRICTION ENDONUCLEASE, HPY 188 III, OBTAINABLE FROM *HELICOBACTER PYLORI* J188 AND A PROCESS FOR PRODUCING THE SAME

BACKGROUND OF THE INVENTION

The present invention relates to a new Type II restriction endonuclease, Hpy188III, obtainable from *Helicobacter pylori* J188, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriciton endonucleases have degenerate or relaxed specificities in that they recognize multiple bases at one or more positions in their recognition sequence, and some restriction endonucleases recognize asymmetric sequences. HaeIII, which recognizes the sequence 5' GGCC 3', is an example of a restriction endonuclease having a symmetrical, non-degenerate recognition sequence, while HaeII, which recognizes 5' (Pu)GCGC(Py) 3' typifies restriction endonucleases having a degenerate or relaxed recognition sequence. Endonucleases with symmetrical recognition sequences generally cleave symmetrically within or adjacent to the recognition site, while those that recognize assymmetric sequences tend to cleave at a distance of from 1 to 18 nucleotides away from the recognition site. Over one hundred twenty-five unique restriction endonucleases have been identified among several thousands of bacterial species that have been examined to date.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (W)GGCC(W) (SEQ ID NO:1), (Pu)GCGC(Py) and GGCC respectively. *Escherichia coli* RY13, on the other hand, synthesizes only one enzyme, EcoRI, which recognizes the sequence GAATTC (SEQ ID NO:2).

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack.

More than 2,500 restriction endonucleases have been isolated from bacterial strains. Of these, more than 1xx recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

There is a continuing need for novel Type II restriction endonucleases. Although Type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Helicobacter pylori* NEB#1174, hereinafter referred to as "Hpy188III", which endonuclease:

(1) recognizes the nucleotide sequence TCNNGA (SEQ ID NO:3) in a double-stranded DNA molecule as shown below, (wherein G represents guanine, C represents cytosine, A represents adenine, T represents thymine and N represents either G, C, A, or T);

(2) cleaves said sequence in the phosphodiester bonds between the C and first N as indicated with the arrows; and (3) cleaves double-stranded PhiX174 DNA to produce 26 fragments, including fragments of 704, 560, 497, 477, 423, 309, 308, 304, 261, 225 basepairs, and 16 fragments smaller than 200 basepairs.

The present invention further relates to a process for the production of the novel restriction endonuclease Hpy188III. This process comprises either culturing *Helicobacter pylori* J188 under conditions suitable for expressing Hpy188III, collecting the cultured cells, obtaining a cell-free extract therefrom and separating and collecting the restriction endonuclease Hpy188III from the cell-free extract, or culturing a transformed host, such as *E. coli*, containing the genes for the Hpy188III methylase and endonuclease, collecting the cultured cells, obtaining a cell-free extract therefrom and separating and collecting the restriction endonuclease Hpy188III from the cell-free extract.

In accordance with the present invention, isoschizomers of Hpy188III have been identified, which are substantially similar to Hpy188III (having greater than about 90% homology at the amino acid level), in other Helicobacter strains, such as *Helicobacter pylori* J178 and *Helicobacter pylori* CH4. Of nine different Helicobacter strains studied, for two of which the DNA sequence is known, it was observed that the genes for various given restriction endonucleases and methylases are present and functional in a number, though not all, of these strains. The presence of Hpy188III or isoschizomers thereof, can be readily assertained in various Helicobacter strains by any of several methods. The genomic DNA of the strain may be prepared (as outlined in the Example below) and digested with the enzyme of the current application. If Hpy188III cleaves the genomic DNA, that strain does not contain an active Hpy188III methyltransferase, whereas if the DNA is not cleaved, it is likely the Hpy188III methyltransferase is present in that strain, and thus potentially the Hpy188III endonuclease as well. The Hpy188III genes may also be obtained form various Helicobacter strains by PCR amplification, using the partial sequence of the Hpy188III methylase gene (SEQ ID NO:4 AND SEQ ID NO:5) provided herein as the guide to PCR primer design. Helicobacter strains containing the enzymes of the present invention may also be identified by the methods exemplified in Schildkraut, *Genetic Engineering*, Volume 6, 117–139, J. K. Setlow and A. Hollaender, eds. (1984), which methods comprise growing cells, obtaining a cell-free extract of proteins from the cells and assaying that extract for the presence of Hpy188III endonuclease activity.

The DNA sequence of clones derived from *Helicobacter pylori* J188 which express the Hpy188III methylase in vivo, as determined by resistance of the clonal plasmids to Hpy188III cleavage, closely matched a region of the genome of the sequenced strains *Helicobacter pylori* J99 and *Helicobacter pylori* 26695. The sequence of various Hpy188III methylase clones matched at the ORF of *Helicobacter pylori* J99 for the gene JHP1012, which was predicted to be a putative DNA methyltransferase of unknown function. The corresponding gene in strain *Helicobacter pylori* 26695, HP0369, was not annotated as a putative methylase, presumably because, due to a frameshift, this ORF designated HP0369 does not contain the N-terminal portion of the Hpy188III methylase gene, which portion includes methylase motif 1, one of the two strongly conserved motifs found in this type of methylase. This observation is consistent with our finding that the genomic DNA from *Helicobacter pylori* 26695 is cleaved by Hpy188III endonuclease, indicating this strain does not have a functional methylase gene protecting against Hpy188III endonuclease action. Genomic DNA from *Helicobacter pylori* J99 is also cleaved by Hpy188III endonuclease, indicating J99 does not have a functional Hpy188III methylase protecting against Hpy188III. This result was more surprising, since the ORF JHP1012 was predicted to encode a functional methylase. We speculate that the functional methylase from *H. pylori* J188 may correspond to both ORFs JHP1012 and JHP 1013, based on the typical size of a gamma-type N6-adenine methylase, thus indicating that strain J99, which is not methylated at Hpy188III sites, has an interrupted Hpy188III methylase gene which was interpreted in the sequence analysis as two separate genes. Whether this speculation is correct or not will become apparent when the DNA sequence of the entire functional Hpy188III gene we have cloned is obtained.

DETAILED DESCRIPTION OF THE INVENTION

Figure 1:
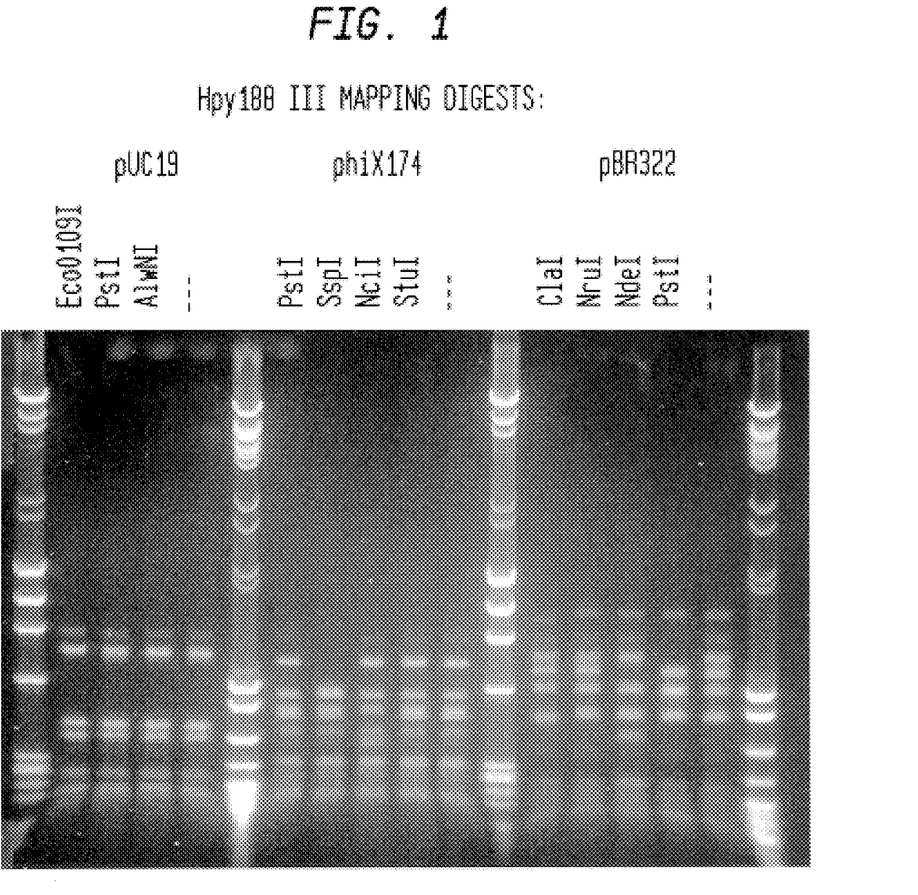
FIG. 1—Agarose gel showing Hpy188III cleavage of various DNAs.

The recognition sequence of the endonuclease of the present invention may be determined by mapping the locations of several Hpy188III cleavage sites in various DNAs and comparing the DNA sequences of these regions for homology, then comparing the predicted cleavage fragments of the putative recognition sequence with the observed restriction fragments produced by Hpy188III cleavage of various DNAs. The endonuclease Hpy188III was found to cleave PhiX174 DNA more than ten times, producing fragments of approximately 700 bp, 550 bp, 500 bp, 475 bp, 420 bp, 300 bp, 250 bp, 225 bp, 200 bp and several smaller fragments. The location of several cut sites were mapped to approximate positions of 425 and 1125 (the 700 bp fragment) and 2700 and 3175 (the 475 bp fragment) by simultaneously digesting PhiX174 DNA with Hpy188III and with endonucleases which cleave at known positions, such as SspI, NciI, StuI and PstI. The approximate size of several of the larger DNA fragments produced by Hpy188III digestion of PhiX174 DNA were entered into the program SITES (Gingeras, et al., Nucl. Acids res. 5: 4105 (1978)), which generates potential recognition sequences for the input data by comparing the fragment sizes which would result from cleavage of the DNA at any given recognition pattern with the input fragment sizes. One such potential pattern generated was TCNNGA, which occurs in PhiX174 DNA at positions consistent with the mapping data obtained, i.e. at positions 422 and 1126, and 2703 and 3180, as well as 22 other sites. The size of fragments predicted from cleavage at TCNNGA sites in PhiX174, pBR322, pUC19, T7 and lambda DNAs matched the observed size of fragments from cleavage of these DNAs with Hpy188III (FIG. 1), from which we conclude that Hpy188III recognizes the sequence 5'-TCNNGA-3'.

The point of cleavage within the Hpy188III recognition sequence may be determined through dideoxy sequencing analysis of the terminal base sequence obtained from Hpy188III cleavage of a suitable DNA substrate (Sanger, F. et al., (1977) *PNAS* 74:5463–5467, Brown, N. L., et al., (1980) *J. Mol. Biol.* 140:143–148.). By the above referenced method (FIG. 2, exemplified in Example II) is was found that Hpy188III cleaves the phosphodiester bond between the C and the first unspecified nucleotide N in the recognition sequence 5'-TC/NNGA-3' (SEQ ID NO:3) to produce a 2 base 5' extension, as indicated by the arrows:

The enzyme of the present invention also has the following properties:

(a) Optimal buffer composition: The optimal buffer tested was NEBuffer 4, supplemented with 100 ug/ml bovine serum albumin. Relative activity in NEBuffer 1 was approximately 70% and NEBuffer 2 was 80%, while relative activity in NEBuffer 3 was approximately 10%.

(b) Heat Inactivation: 4 units of Hpy188III in 50 μl NEBuffer 4 can be inactivated in twenty minutes at 65° C.

In accordance with the present invention, Hpy188III is obtained by culturing *Helicobacter pylori* strain NEB#1174 and recovering the endonuclease from the cells. A sample of *Helicobacter pylori* NEB#1174 has been deposited under the terms and conditions of the Budapest Treaty at the American Type Culture Collection (ATCC) on, Jan. 3, 2001 and bears the ATCC Accession No. PTA-2878 Hpy188III endonuclease may also be obtained from other, presumably closely related, *Helicobacter pylori* strains, such as Helicobacter pylori J178 (NEB#1241) or *Helicobacter pylori* CH4 (NEB#1236, ATCC Accession No. PTA-781).

For recovering the enzyme of the present invention *Helicobacter pylori* may be grown using any suitable technique. For example, *Helicobacter pylori* J188 may be grown in Brucella broth media (BBL Microbiology Systems, Cockeysville, Md.) incubated anaerobically under 5% carbon dioxide at 37° C. Cells in the late logarithmic stage of growth are collected by centrifugation and either disrupted immediately or stored frozen at −70° C. The Hpy188 III enzyme can be isolated from *Helicobacter pylori* cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing Hpy188III. The Hpy188III endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed by Wilson, et al., U.S. Pat. No. 5,200,333. As an example, DNA from a bacterial strain which contains an R-M system, such as *Helicobacter pylori*, is purified, partially digested with suitable Type II endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

PRODUCTION OF Hpy188III ENDONUCLEASE

*Helicobacter pylori* strain NEB#1174 was grown in Brucella broth media (BBL Microbiology Systems, Cockeysville, Md.) incubated anaerobically under 5% carbon dioxide at 37° C. The cells were harvested by centrifugation and stored frozen at −70° C.

4 grams of the cells obtained above were suspended in 25 ml buffer A (20 mM Tris-HCl, 0.1 mM EDTA, 1 mM dithiothreitol, 5% glycerol, pH 7.6 at 10° C.) adjusted to 50 mM NaCl. The cell suspension was sonicated four cycles of two minutes sonication followed by two minutes cooling in an ice-water bath until approximately 12 mg protein per gram of cells was released. The lysate was centrifuged at 15,000 rpm for 20 minutes at 4° C. in a Beckman JA17 rotor. 26 ml of supernatant was obtained containing approximately 320 mg of soluble protein.

The supernatant solution was applied to a 5 ml Heparin-HiTrap column (Pharmacia, Piscataway, N.J.) equilibrated in buffer A adjusted to 50 mM NaCl. A 10 ml wash of buffer A adjusted to 50 mM NaCl was applied, then a 50 ml gradient of NaCl from 50 mM to 1M in buffer A was applied and fractions of 1.5 ml were collected. Fractions were tested for Hpy188 III activity, as described below. Hpy188III activity eluted at approximately 0.4 to 0.5 M NaCl.

The Heparin-HiTrap column fractions containing the Hpy188III activity were pooled, diluted to approximately 100 mM NaCl in buffer A and applied to a 3 ml Heparin-TSK column (Toso-Haas, Philadelphia, Pa.) equilibrated in buffer A adjusted to 100 mM NaCl. The column was washed with 5 mls buffer A adjusted to 100 mM NaCl. The protein solution was eluted with a 50 ml gradient of 100 mM to 1M NaCl in buffer A and 1 ml fractions were collected. The Hpy188III activity eluted at approximately 0.32M NaCl. 6 fractions which contained Hpy188III activity were pooled and diluted in buffer A to approximately 50 mM NaCl.

The diluted enzyme solution was applied to a 1 ml Mono-Q column (Pharmacia) equilibrated in buffer A adjusted to 50 mM NaCl. The column was washed with 2.5 ml buffer A adjusted to 50 mM NaCl and the Hpy188III enzyme was eluted with a 40 ml gradient of 50 mM to 0.6 M NaCl in buffer A. The Hpy188III activity eluted at approximately 0.28 M NaCl. A 2 ml pool of Hpy188III containing approximately 500 units of Hpy188III activity was collected. The Hpy188III obtained was substantially pure and free of contaminating endonuclease and exonuclease activities. Bovine serum albumin was added as a stabilizer to a final concentration of 200 ug/ml and the Hpy188III was dialyzed against storage buffer (50% glycerol, 50 mM NaCl, 20 mM Tris-HCl, 0.1 mM dithiothreitol, pH 7.5).

Activity Determination

Hpy188III activity: Samples of from 1 to 10 μl were added to 50 μl of substrate solution consisting of 1× NEBuffer 4 containing 1 ug Lambda phage DNA. The reaction was incubated at 37° C. for 5 to 60 mins. The reaction was terminated by adding 15 μl of a stop solution (50% glycerol, 50 mM EDTA pH 8.0, and 0.02% Bromophenol Blue). The reaction mixture was applied to a 1.2% agarose gel and electrophoresed. The bands obtained were identified in comparison with DNA size standards.

Unit Definition: One unit of Hpy188III is defined as the amount of Hpy188III required to completely cleave 1.0 µg of Lambda DNA in a total reaction volume of 50 µl NEBuffer 4, within one hour at 37° C.

Optimal Buffer Conditions: For optimum Hpy188III activity NEBuffer 4 (50 mM potassium acetate, 20 mM Tris-acetate, 10 mM magnesium acetate, 1 mM dithiothreitol (pH 7.9 at 25° C.)) was used.

EXAMPLE II

DETERMINATION OF THE Hpy188III CLEAVAGE SITE

The location of Hpy188III cleavage relative to the recognition sequence was determined by cleavage of a primer extension product, which was then electrophoresed alongside a set of standard dideoxy sequencing reactions produced from the same primer and template. M13mp18 single-stranded DNA was employed as the template because there is an Hpy188III recognition site at position 1300 conveniently located 107 bp 3' of a priming site for a primer designated M13 Q1-Q2 (5'-dGGTCGCTGAGGCTTGCAGGG-3' (SEQ ID NO:6)).

Sequencing Reactions:

The sequencing reactions were performed using the Sequenase version 2.0 DNA sequencing kit (Amersham Life Science) with modifications for the cleavage site determination. The template and primer were assembled in a 0.5 mL eppendorf tube by combining 10 µl dH20, 4 µl 5× sequencing buffer (200 mM Tris pH 7.5, 250 mM NaCl, 100 mM MgCl$_2$), 4 µl M13mp18 single stranded DNA (2 µg) and 2 µl of primer (M13 Q1-Q2 at 3.2 µM concentration). The solution was incubated at 65° C. for 2 minutes, then cooled to 37° C. over 20 minutes in a beaker of 65° C. water on the benchtop to anneal the primer. The labeling mix and T7 Sequenase were diluted according to manufacturer's instructions. The annealed primer and template tube was placed on ice. To this tube were added 2 µl 100 mM DTT, 4 µl diluted dGTP labeling mix, 1 µl [α-$^{33}$P] dATP (2000Ci/mmole, 10mCi/ml) and 4 µl diluted T7 Sequenase polymerase. The reaction was mixed and incubated at room temperature for 5 minutes. 3.5 µl of this reaction was then transferred into each of four tubes containing 2.5 µl termination mix for the A, C, G and T sequencing termination reactions. To the remaining reaction was added to 17 µl of Sequence Extending Mix, which is a mixture of dNTPs (no ddNTPs) to allow extension of the primer through and well beyond the Hpy188III site with no terminations to create a labeled strand of DNA extending through the Hpy188III recognition site for subsequent cleavage. The reactions were incubated 5 minutes at 37° C. To the A, C, G and T reactions were added 4 µl of stop solution and the samples were stored on ice. The extension reaction was then incubated at 70° C. for 20 minutes to inactivate the DNA polymerase (Sequenase), then cooled on ice. 9.5 µl of the extension reaction was placed in one 0.5 ml eppendorf tube and 6.5 µl were placed in a second tube. To the 9.5 µl tube was added 1 µl (approximately 1 unit) Hpy188III endonuclease. The reaction was mixed and 2 µl were transferred to the second tube. The enzyme digest reactions were incubated at 37° C. for 30 minutes. Following digestion 4 µl of the reactions were removed and mixed with 4 µl stop solution (the minus polymerase reaction). To the remaining approximately 4 µl was added 0.2 µl (1 unit) Klenow fragment DNA polymerase (NEB#210) containing 40 µM dNTPs and the reaction was incubated at room temperature for 15 minutes, after which 4 µl of stop solution was added (the plus polymerase reaction). The enzyme digest reactions were also stored on ice prior to electrophoresis. The reaction products were electrophoresed on an 6% Bis-Acrylamide sequencing gel, with the Hpy188III digestions of the extension reaction next to the set of sequencing reactions produced from the same primer and template combination.

Figure 2:
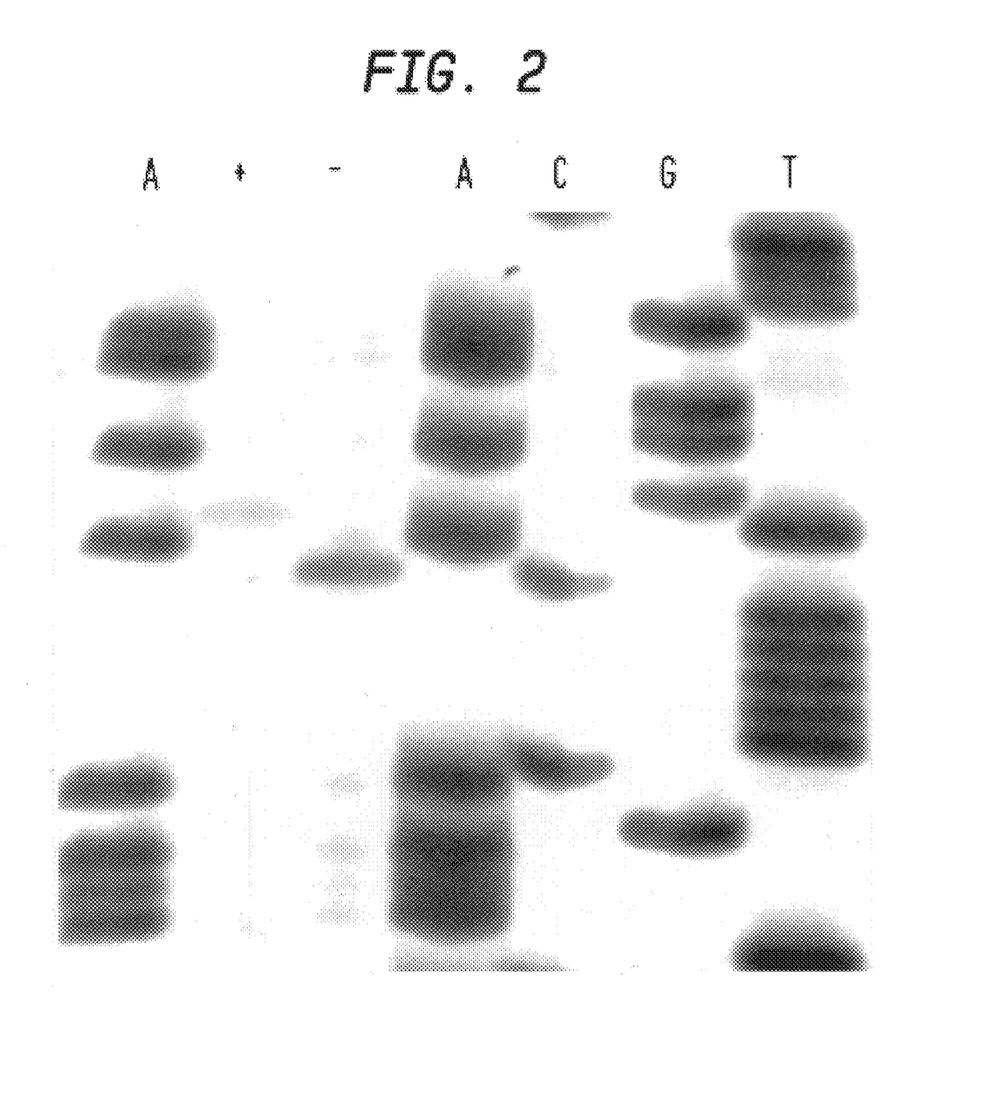
FIG. 2—Determination of the Hpy188III cleavage site.

Results:

Digestion of the extension reaction product with Hpy188III endonuclease (the minus reaction) produced a band which co-migrated with the second nucleotide (the C) of the Hpy188III recognition sequence 5'-TCNNGA-3', indicating cleavage between the C and the first N of the recognition sequence (FIG. 2). Treatment with Klenow fragment DNA polymerase following Hpy188III digestion produced a fragment which co-migrated with the second unspecified nucleotide in the Hpy188III recognition sequence TCNNGA, indicating cleavage on the opposite strand of DNA between the C and first unspecified nucleotide (N) of the recognition sequence. These results indicate Hpy188III cleaves DNA between the C and first N in its recognition sequence on both DNA strands, 5'-TC↓NNGA-3', to produce a two base 5' extension.

EXAMPLE III

CLONING THE Hpy188III Endonuclease and Methylase

1. DNA purification: To prepare the genomic DNA of *Helicobacter pylori* J188, 1 gram of cell paste was resuspended in 10 ml of 25% sucrose, 0.05 M Tris-HCl pH 8.0, to which was added 5 ml of 0.25 M EDTA, pH 8.0. Then 3 ml of lysozyme solution (10 mg/ml lysozyme in 0.25 M Tris-HCl, pH 8.0) was added and the cell suspension was incubated at 4° C. for 16 hours. 12 ml of Lytic mix (1% Triton-X100, 0.05 M Tris, 62 mM EDTA, pH 8.0) and 2.5 ml of 10% SDS was then added and the solution was incubated at 37° C. for 5 minutes. The solution was extracted with one volume of equilibrated phenol:chloroform:isoamyl alcohol (50:48:2, v/v/v) and the aqueous phase was recovered and extracted with one volume of chloroform:isoamyl alcohol (24:1, v/v) two times. The aqueous solution was then dialysed against four changes of 2 L of 10 mM Tris, 1 mM EDTA, pH 8.0. The dialysed DNA solution was digested with RNase (100 µg/ml) at 37° C. for 1 hour. The DNA was precipitated by the addition of 1/10th volume 5 M NaCl and 0.55 volumes of 2-propanol and spooled on a glass rod. The DNA was briefly rinsed in 70% ethanol, air dried and dissolved in 4 ml TE (10 mM Tris, 1 mM EDTA, pH 8.0) to a concentration of approximately 250 µg/ml and stored at 4° C.

2. Construction of libraries of genomic *Helicobacter pylori* J188 DNA in a selectable vector:

*Helicobacter pylori* J188 genomic DNA was partially digested with either of two frequent cutting enzymes, Sau3AI or AciI. The partial digestion was carried out by serial dilution of the Sau3AI or the AciI restriction endonuclease from 0.5 units/µg DNA to 0.016 units/µg in the manufacturer's reaction buffer and digesting at 37° C. for 1 hour. The reactions were subsequently terminated by phenol:chloroform extraction. Reactions which produced an average size range of fragments from 2 to 8 kb were used for library construction. 3 µg of this partially digested Hpy188III genomic DNA was ligated to 1 µg of the vector pUC19 (previously cleaved by BamHI (Sau3AI) or AccI (AciI) and dephosphorylated with calf intestinal alkaline phosphatase) in a final volume of 50 µl in 1× NEB ligase buffer with 1000 units (NEB) of T4 DNA ligase. The ligation reactions were incubated at 16° C. for 16 hours. 10 ul of the each ligation reaction mixture was then transformed by electroporation into E. coli ER2683 cells and grown out in 10 ml L-Broth for 1 hour. 10 µl was then plated onto L-Broth agar plates supplemented with 100 µg/ml ampicillin to count the number of insert containing transformants and the plates were incubated at 37° C. overnight. The remaining outgrowth was grown overnight in 250 ml L-Broth supplemented with 100 µg/ml ampicillin with shaking at 37° C. A total of 1×10$^6$ individual transformants were obtained for the Sau3AI library, and 6×10$^5$ transformants for the AciI library. The cells of the 250 ml liquid culture were harvested by centrifugation at 5 K rpm for 5 minutes. The plasmids from these cells were purified by a standard alkaline lysis procedure, followed by four rounds of desalting in an Amicon Centricon-50 microconcentration device, washing with TE buffer each round, and then the plasmids were precipitated by PEG precipitation (combined 672 µl centricon purified plasmid, 128 µl 5 M NaCl and 800 µl 13% PEG-8000, incubated at 4° C. for 30 min, microfuged at 4° C. at maximum speed for 10 minutes, washed 2× with 70% cold ethanol) and resuspended in TE buffer at a concentration of 250 µg/ml.

3. Hpy188III methylase selection: 1 µg of the plasmid library was digested for 16 hours at 37° C. in 50 µl 1× NEB#4 buffer with 3, 1, 0.3 and 0.1 units of the Hpy188III prepared as above from H. pylori J188 cells. 10 µl of the Hpy188III digestion reaction was then transformed into 100 µl E. coli ER2688 competent cells and plated on L-broth plates containing 100 µg/ml ampicillin and the plates were incubated at 37° C. overnight. A total of 4 transformants were obtained from the Sau3AI library 3 unit digestion and 75 transformants were obtained from the Sau3AI library 1 unit digestion. Twenty of the surviving clones from the Sau3AI library were analyzed as follows: Plasmid from each colony was isolated by miniprep procedures and digested with Hpy188III endonuclease.

Analysis of plasmid clones: Individual transformants were inoculated into 10 ml cultures of L-broth containing 100 µg/ml ampicillin, grown overnight at 37° C. with shaking, and the plasmids that they carried were prepared by Qiagen QIAprep® Spin Miniprep columns according to the manufacturers instructions. Plasmids were assayed for the presence of the Hpy188III methylase by digestion with Hpy188III endonuclease.

10 of 20 clones analyzed were found to be protected from Hpy188III digestion; four were partially protected and 6 fully protected. Further restriction analysis showed these clones contained common Sau3AI and PstI restriction fragments. Six of the clones were tested for Hpy188III restriction activity when grown in L-Broth containing 100 µg/ml ampicillin, but no endonuclease activity was observed.

EXAMPLE IV

SEQUENCING THE Hpy188III ENDONUCLEASE AND METHYLASE

Figure 3:
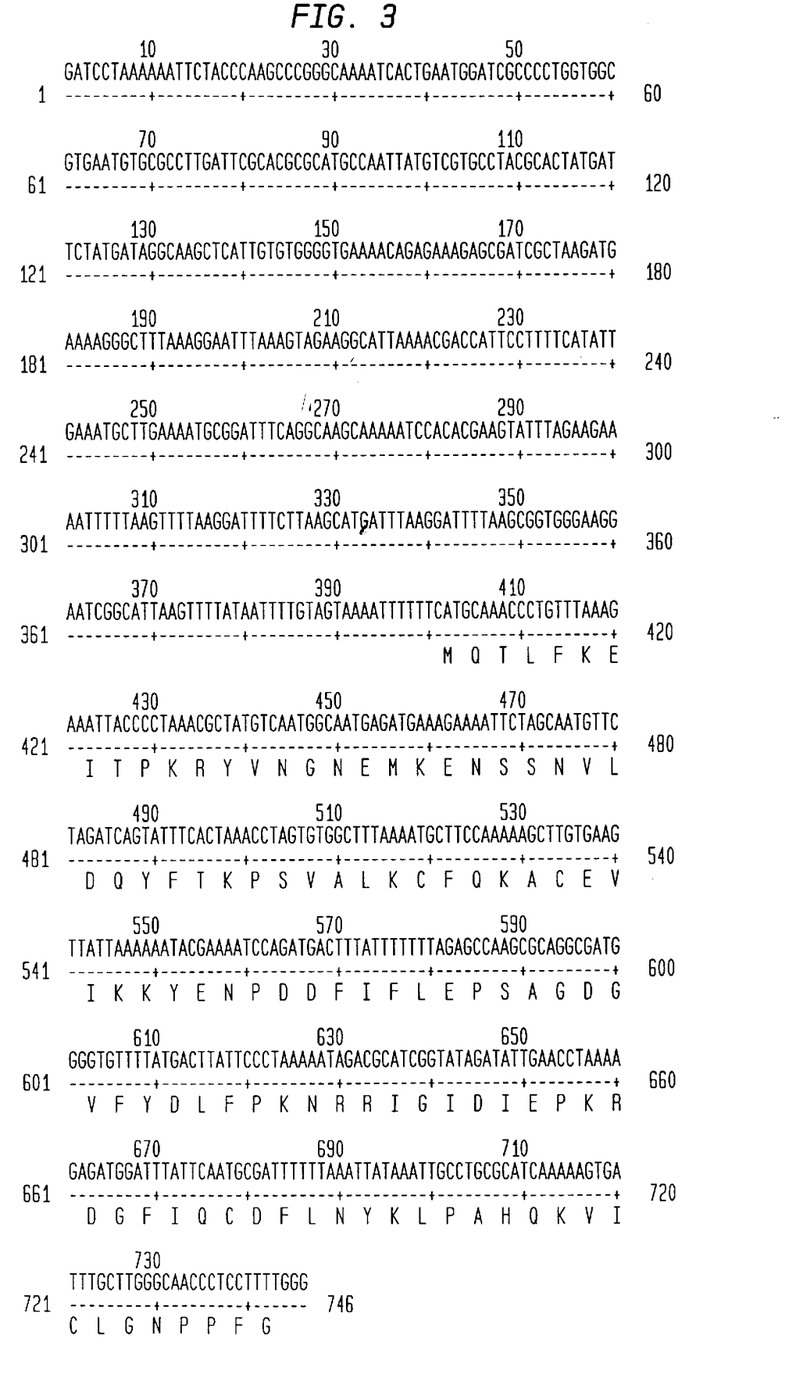
FIG. 3—DNA (SEQ ID NO:4) and Amino Acid (SEQ ID NO:5) sequence from an Hpy188III methylase expressing clone.

DNA Sequencing: DNA sequencing was performed on double-stranded templates on an ABI automated sequencer. Individual clones were sequenced from primers located in the vector on both sides of the inserts. The DNA sequencing of the clones was incomplete at time of filing. Computer analyses of the DNA sequences obtained were performed with the Genetics Computer Group programs (Deverenx, et al., Nucleic Acids Res. 12:387–395 (1984)) and database similarity searches were performed via the internet at the National Center for Biotechnology Information site (http://www.ncbi.nlm.nih.gov/BLAST/) using the BLASTX algorithm (Altschul, et al., J. Mol. Biol 215:403–410 (1990) and Gish, et al., Nature Genet. 3:266–722 (1993)). A part of an open reading frame (ORF) bp which contained motifs characteristic of the gamma type N$^6$-methyl adenine DNA methyl-transferases was identified, which orf is believed to be the Hpy188III methyl-transferase. The motifs identified were motif I: amino acid sequence -FLEPSAGDGVFY- (SEQ ID NO:7) and motif 4: amino acid sequence -GNPPF- (SEQ ID NO:8). The DNA nucleotide sequence from the end of the cloned insert DNA reading into the methylase gene for one of the clones is shown in FIG. 3.

What is claimed is:

1. Isolated DNA coding for the Hpy188III restriction methyltransferase, wherein the isolated DNA is obtainable from *Helicobacter pylori* J188.

2. A recombinant DNA vector comprising a vector into which a DNA segment coding for the methyltransferase has been inserted.

3. Isolated DNA coding for the Hpy188III methyltransferase, wherein the isolated DNA is obtainable from ATCC Accession No. PTA-2878.

4. A vector which comprises the isolated DNA of claim 3.

5. A host cell transformed by the vector of claim 2 or 4.

6. A method of producing the Hpy188III methyltransferase comprising culturing a host cell transformed with the vector of claim 2 or 4 under conditions suitable for expression of said methyltransferase.

7. A substantially pure Type II restriction endonuclease obtainable from *Helicobacter pylori* (ATCC Accession No. PTA-2878) recognizing the following base sequence in double-stranded deoxyribonucleic acid molecules:

5'-TC↓NNGA-3'

3'-AGNN↑CT-5' and having a cleavage position defined by the arrows.

8. A method for obtaining the Type II restriction endonuclease of claim 7, comprising cultivating a sample of *Helicobacter pylori* under conditions favoring the production of said endonuclease and separating said endonuclease therefrom.

9. The Type II restriction endonuclease of claim 7, wherein the restriction endonuclease is purified form *Helicobacter pyloi* J188 (ATCC Accession No. PTA-2878).

10. An isolated Type II restriction endonuclease with 90% or greater amino acid sequence identity to the Type II restriction endonuclease of claim 7, obtainable from Helicobacter species.

* * * * *

UNITED STATES PATENT AND TRADEMARK OFFICE
CERTIFICATE OF CORRECTION

PATENT NO. : 6,238,901 B1
DATED : May 29, 2001
INVENTOR(S) : Richard D. Morgan and Qing Xu It is certified that error appears in the above-identified patent and that said Letters Patent is hereby corrected as shown below:

Title page,
Column 1,
Line 1, before "TYPE" insert -- A NOVEL --

Column 5,
Line 14, replace "on," " with -- on --

Column 14,
Line 59, "*pyloi*" with -- *pylori* --

Column 1,
Line 43, replace "assymmetric" with -- asymmetric --
Line 51, replace "example" with -- example, --
Line 64, replace "ecule" with -- ecules --

Column 2,
Line 20, replace "1xx" with -- 200 --

Column 3,
Line 28, replace "form" with -- from --

Column 4,
Line 37, replace "res." with -- Res. --
Line 57, replace "is" with -- it --

Column 5,
Line 19, replace "invention" with -- invention, --

Column 7,
Line 32, replace "dH2O" with -- $dH_2O$ --
Line 48, after "added" delete "to"

UNITED STATES PATENT AND TRADEMARK OFFICE
CERTIFICATE OF CORRECTION

PATENT NO.  : 6,238,901 B1
DATED       : May 29, 2001
INVENTOR(S) : Richard D. Morgan and Qing Xu It is certified that error appears in the above-identified patent and that said Letters Patent is hereby corrected as shown below:

Column 8,
Line 6, replace "an" with -- a --

Column 9,
Line 4, after "of" delete "the"
Line 9, replace "insert" with -- inserts --

Signed and Sealed this

Eleventh Day of December, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,238,901 B1  Page 1 of 1
DATED : May 29, 2001
INVENTOR(S) : Morgan et al.

It is certified that error appears in the above-identified patent and that said Letters Patent is hereby corrected as shown below:

<u>Column 1,</u>
Line 6, insert -- This invention was made with Government support under contract number DK53707 awarded by the National Institutes of Health. The Government has certain rights in the invention. --

Signed and Sealed this

Twenty-eighth Day of January, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 6
<212> TYPE: DNA
<213> ORGANISM: Haemophilus aegyptius

<400> SEQUENCE: 1 wggccw                                                          6

<210> SEQ ID NO 2
<211> LENGTH: 6
<212> TYPE: DNA
<213> ORGANISM: Escherichia coli

<400> SEQUENCE: 2 gaattc                                                          6

```
<210> SEQ ID NO 3
<211> LENGTH: 6
<212> TYPE: DNA
<213> ORGANISM: Helicobacter pylori
<220> FEATURE:
<223> OTHER INFORMATION: At positions 3 and 4, N= G, A, C or T

<400> SEQUENCE: 3 tcnnga                                                                    6

<210> SEQ ID NO 4
<211> LENGTH: 746
<212> TYPE: DNA
<213> ORGANISM: Helicobacter pylori
<220> FEATURE:
<221> NAME/KEY: CDS
<222> LOCATION: (402)..(746)

<400> SEQUENCE: 4
gatcctaaaa aattctaccc aagcccgggc aaaatcactg aatggatcgc ccctggtggc         60
gtgaatgtgc gccttgattc gcacgcgcat gccaattatg tcgtgcctac gcactatgat        120
tctatgatag gcaagctcat tgtgtgggt gaaaacagag aaagagcgat cgctaagatg         180
aaaagggctt taaggaatt taaagtagaa ggcattaaaa cgaccattcc ttttcatatt         240
gaaatgcttg aaaatgcgga tttcaggcaa gcaaaaatcc acacgaagta tttagaagaa        300 aattttaag ttttaaggat tttcttaagc atgatttaag gatttaagc ggtgggaagg          360 aatcggcatt aagttttata attttgtagt aaaattttt c atg caa acc ctg ttt         416
                                            Met Gln Thr Leu Phe
                                              1               5 aaa gaa att acc cct aaa cgc tat gtc aat ggc aat gag atg aaa gaa         464
Lys Glu Ile Thr Pro Lys Arg Tyr Val Asn Gly Asn Glu Met Lys Glu
             10                  15                  20 aat tct agc aat gtt cta gat cag tat ttc act aaa cct agt gtg gct         512
Asn Ser Ser Asn Val Leu Asp Gln Tyr Phe Thr Lys Pro Ser Val Ala
         25                  30                  35 tta aaa tgc ttc caa aaa gct tgt gaa gtt att aaa aaa tac gaa aat         560
Leu Lys Cys Phe Gln Lys Ala Cys Glu Val Ile Lys Lys Tyr Glu Asn
     40                  45                  50 cca gat gac ttt att ttt tta gag cca agc gca ggc gat ggg gtg ttt         608
Pro Asp Asp Phe Ile Phe Leu Glu Pro Ser Ala Gly Asp Gly Val Phe
 55                  60                  65 tat gac tta ttc cct aaa aat aga cgc atc ggt ata gat att gaa cct         656
Tyr Asp Leu Phe Pro Lys Asn Arg Arg Ile Gly Ile Asp Ile Glu Pro
 70                  75                  80                  85 aaa aga gat gga ttt att caa tgc gat ttt tta aat tat aaa ttg cct         704
Lys Arg Asp Gly Phe Ile Gln Cys Asp Phe Leu Asn Tyr Lys Leu Pro
                 90                  95                 100 gcg cat caa aaa gtg att tgc ttg ggc aac cct cct ttt ggg                 746
Ala His Gln Lys Val Ile Cys Leu Gly Asn Pro Pro Phe Gly
                105                 110                 115

<210> SEQ ID NO 5
<211> LENGTH: 115
<212> TYPE: PRT
<213> ORGANISM: Helicobacter pylori

<400> SEQUENCE: 5

Met Gln Thr Leu Phe Lys Glu Ile Thr Pro Lys Arg Tyr Val Asn Gly
  1               5                  10                  15

Asn Glu Met Lys Glu Asn Ser Ser Asn Val Leu Asp Gln Tyr Phe Thr
             20                  25                  30
```

-continued

```
Lys Pro Ser Val Ala Leu Lys Cys Phe Gln Lys Ala Cys Glu Val Ile
        35                  40                  45

Lys Lys Tyr Glu Asn Pro Asp Asp Phe Ile Phe Leu Glu Pro Ser Ala
        50                  55                  60

Gly Asp Gly Val Phe Tyr Asp Leu Phe Pro Lys Asn Arg Arg Ile Gly
 65                  70                  75                  80

Ile Asp Ile Glu Pro Lys Arg Asp Gly Phe Ile Gln Cys Asp Phe Leu
                 85                  90                  95

Asn Tyr Lys Leu Pro Ala His Gln Lys Val Ile Cys Leu Gly Asn Pro
            100                 105                 110

Pro Phe Gly
        115

<210> SEQ ID NO 6
<211> LENGTH: 20
<212> TYPE: DNA
<213> ORGANISM: Helicobacter pylori

<400> SEQUENCE: 6
ggtcgctgag gcttgcaggg                                                 20

<210> SEQ ID NO 7
<211> LENGTH: 12
<212> TYPE: PRT
<213> ORGANISM: Helicobacter pylori

<400> SEQUENCE: 7

Phe Leu Glu Pro Ser Ala Gly Asp Gly Val Phe Tyr
 1               5                  10

<210> SEQ ID NO 8
<211> LENGTH: 5
<212> TYPE: PRT
<213> ORGANISM: Helicobacter pylori

<400> SEQUENCE: 8

Gly Asn Pro Pro Phe
 1               5
```